(12) United States Patent
Goldshtein et al.

(10) Patent No.: US 11,642,084 B2
(45) Date of Patent: May 9, 2023

(54) MEASUREMENT OF BODY FLUID RETENTION USING INDUCTIVE COUPLING

(71) Applicant: Vectorious Medical Technologies Ltd., Tel-Aviv (IL)

(72) Inventors: Oren Goldshtein, Nahariya (IL); Matan Hershko, Kiryat Ata (IL)

(73) Assignee: VECTORIOUS MEDICAL TECHNOLOGIES LTD., Tel Aviv (IL)

( * ) Notice: Subject to any disclaimer, the term of this patent is extended or adjusted under 35 U.S.C. 154(b) by 557 days.

(21) Appl. No.: 16/809,618

(22) Filed: Mar. 5, 2020

(65) Prior Publication Data
US 2021/0275733 A1    Sep. 9, 2021

(51) Int. Cl.
A61B 5/00      (2006.01)
G01R 33/00    (2006.01)
A61B 5/0215  (2006.01)
A61B 5/05      (2021.01)

(52) U.S. Cl.
CPC .......... *A61B 5/6869* (2013.01); *A61B 5/0215* (2013.01); *A61B 5/05* (2013.01); *A61B 5/4875* (2013.01); *G01R 33/0094* (2013.01); *A61B 5/7225* (2013.01); *A61M 2205/04* (2013.01)

(58) Field of Classification Search
CPC ....... A61B 5/6869; A61B 5/0215; A61B 5/05; A61B 5/4875; A61B 5/7225; A61B 5/0535; A61B 5/02; A61B 5/02028; A61B 5/0263; A61B 5/0265; G01R 33/0094; G01R 33/02; A61M 2205/04
See application file for complete search history.

(56) References Cited

U.S. PATENT DOCUMENTS

| | | | |
|---|---|---|---|
| 9,788,752 B2 | 10/2017 | Weinstein et al. | |
| 10,105,103 B2 | 10/2018 | Goldshtein et al. | |
| 10,205,488 B2 | 2/2019 | Hershko et al. | |
| 2008/0077016 A1* | 3/2008 | Sparks | A61B 5/0031 600/459 |
| 2013/0060103 A1 | 3/2013 | Bergida et al. | |
| 2015/0282720 A1 | 10/2015 | Goldshtein et al. | |
| 2018/0098772 A1 | 4/2018 | Goldshtein et al. | |
| 2018/0110468 A1 | 4/2018 | Goldshtein et al. | |
| 2018/0262037 A1* | 9/2018 | Meskens | H02J 50/402 |
| 2019/0008401 A1 | 1/2019 | Goldshtein et al. | |
| 2020/0305759 A1* | 10/2020 | Barash | A61B 5/4836 |

FOREIGN PATENT DOCUMENTS

| | | | |
|---|---|---|---|
| WO | 2018122837 A1 | 7/2018 | |
| WO | WO-2019094877 A1 * | 5/2019 | ......... A61B 5/02042 |

* cited by examiner

*Primary Examiner* — Eric F Winakur
*Assistant Examiner* — Emily C Clement
(74) *Attorney, Agent, or Firm* — Kligler & Associates Patent Attorneys Ltd

(57) ABSTRACT

An apparatus includes a magnetic-field transducer, and circuitry. The magnetic-field transducer is configured to be coupled externally to a body of a patient. The circuitry is configured to generate and apply to the magnetic-field transducer a time-varying signal, so as to generate a time-varying magnetic field outside the body of the patient, for supplying electrical energy by inductive coupling to an electronic device that is positioned inside the body, to estimate an intensity of the magnetic field that reaches the electronic device, and to assess fluid retention in an organ of the patient based on the estimated intensity of the magnetic field.

20 Claims, 5 Drawing Sheets

MEASUREMENT OF BODY FLUID RETENTION USING INDUCTIVE COUPLING

FIELD OF THE INVENTION

The present invention relates generally to medical devices, and particularly to methods and systems for assessing body fluid retention using inductive coupling.

BACKGROUND OF THE INVENTION

Heart Failure (HF) is a chronic, life-threatening condition that is one of the leading causes of death worldwide. HF develops when the heart's pumping action becomes inefficient, causing increased retention of body fluids. The latter may result in shortness of breath, fatigue, edema, and often causes frequent hospitalizations. HF significantly impacts the patient's quality of life, and may become fatal. In many cases HF can be managed, and fatal episodes prevented, provided that reliable indications from the patient's body are available.

Various techniques have been proposed for detecting excessive body fluid retention. For example, PCT International Publication WO 2018/122837 describes a system for Radio-Frequency (RF) tissue monitoring. The system includes an internal probe for transmitting and/or receiving an RF signal, an external probe for transmitting and/or receiving an RF signal, and a processing unit. The external probe is set to be positioned in a location outside the body, and the internal probe is set to be mounted on an elongated guiding element set for insertion via the pharynx into a tract of the patient. The processing unit is configured to analyze an RF signal transmitted between the internal probe and the external probe, propagating via tissue of the patient between walls of the tract and a skin layer of the patient, and to estimate at least one dielectric property of the tissue.

As another example, U.S. Patent Application Publication 2013/0060103 describes a system for monitoring biological tissue of a patient. The system includes an implantable intrabody probe and an extrabody probe which propagate an electromagnetic (EM) signal, using an antenna, via tissue therebetween. A processing unit analyzes the EM signal to detect a change in at least one biological parameter of the tissue, and an output unit outputs the change. The systems and methods in some embodiments allow performing real-time signal analysis for detecting and/or monitoring dielectric properties and/or dielectric related changes in pulmonary tissues, for instance due to fluid accumulation.

As yet another example, U.S. Pat. No. 9,788,752 describes an implantable dielectrometer that includes a sealed case configured for implantation within a body of a human subject. A dielectrometric probe is connected to the case and includes first and second conductors, which are configured to be placed in proximity to target tissue in the body. A driving circuit, which is contained in the case, is coupled to apply an RF signal to the probe and to sense the signal returned from the probe. Processing circuitry is configured to evaluate, responsively to the returned signal, a dielectric property of the target tissue. A water content assumption can be estimated based on a multi-material liquid model.

SUMMARY OF THE INVENTION

An embodiment of the present invention that is described herein provides an apparatus including a magnetic-field transducer, and circuitry. The magnetic-field transducer is configured to be coupled externally to a body of a patient. The circuitry is configured to generate and apply to the magnetic-field transducer a time-varying signal, so as to generate a time-varying magnetic field outside the body of the patient, for supplying electrical energy by inductive coupling to an electronic device that is positioned inside the body, to estimate an intensity of the magnetic field that reaches the electronic device, and to assess fluid retention in an organ of the patient based on the estimated intensity of the magnetic field.

In an embodiment, the circuitry is configured to initiate a responsive action upon detecting that the fluid retention is indicative of an abnormality. In a disclosed embodiment, the organ is a lung of the patient.

In some embodiments, the circuitry is configured to receive, from the electronic device, data indicative of the intensity of the magnetic field that reaches the electronic device, and to estimate the intensity based on the data. In an example embodiment, the data includes an indication of whether the intensity of the magnetic field exceeds a predefined threshold. In an embodiment, the circuitry is configured to assess the fluid retention by adaptively adjusting a power level of the magnetic field applied to the magnetic-field transducer depending on the data.

In another embodiment, the circuitry is configured to assess the fluid retention by adaptively adjusting a power level of the magnetic field applied to the magnetic-field transducer, and identifying a minimal power level that invokes a response from the electronic device. In yet another embodiment, the electronic device transfers data to outside the body by modulating the induction-coupled magnetic field, and the circuitry is configured to estimate the intensity of the magnetic field that reaches the electronic device by measuring the modulated magnetic field outside the body. In still another embodiment, the electronic device transfers a value to outside the body by resonating at a frequency that is indicative of the value, and the circuitry is configured to estimate the intensity of the magnetic field that reaches the electronic device by measuring the magnetic field outside the body while the electronic device is resonating.

In some embodiments, the circuitry is configured to receive from the electronic device one or more blood pressure measurements in a heart of the patient, and to initiate a responsive action upon detecting that a combination of the fluid retention and the blood pressure measurements is indicative of an abnormality.

There is additionally provided, in accordance with an embodiment of the present invention, a system including a transformer and circuitry. The transformer includes a primary coil and a secondary coil. One of the primary coil and the secondary coil is configured to be positioned inside a body of a patient, and the other of the primary coil and the secondary coil is configured to be positioned externally to the body. The circuitry is configured to estimate a measure of magnetic-field inductive-coupling between the primary coil and the secondary coil of the transformer, and to assess fluid retention in an organ of the patient based on the estimated measure of the magnetic-field inductive-coupling.

There is also provided, in accordance with an embodiment of the present invention, a method including generating and applying a time-varying signal to a magnetic-field transducer coupled externally to a body of a patient, so as to generate a time-varying magnetic field outside the body of the patient, for supplying electrical energy by inductive coupling to an electronic device that is positioned inside the body. An intensity of the magnetic field that reaches the electronic device is estimated. Fluid retention in an organ of the patient is assessed based on the estimated intensity of the magnetic field.

There is further provided, in accordance with an embodiment of the present invention, a method including estimating a measure of magnetic-field inductive-coupling between a primary coil and a secondary coil of a transformer, wherein one of the primary coil and the secondary coil is positioned inside a body of a patient, and the other of the primary coil and the secondary coil is positioned externally to the body. Fluid retention in an organ of the patient is assessed based on the estimated measure of the magnetic-field inductive-coupling.

The present invention will be more fully understood from the following detailed description of the embodiments thereof, taken together with the drawings in which:

DETAILED DESCRIPTION OF EMBODIMENTS

Overview

Figure 1:
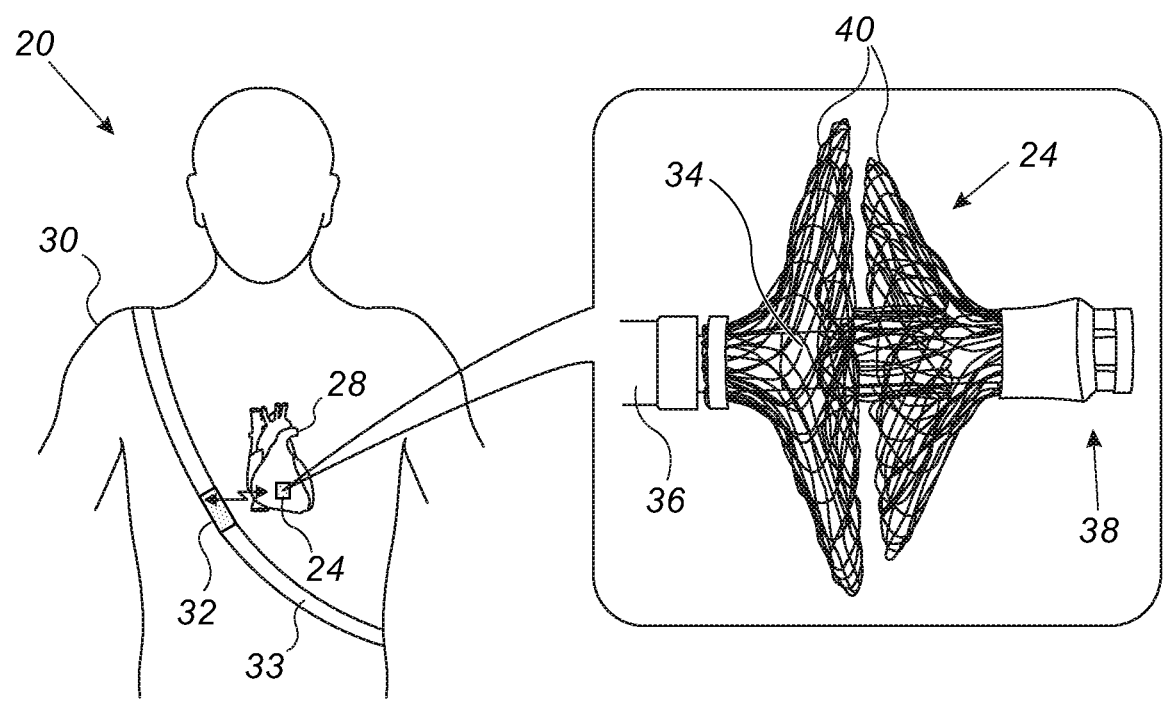
FIG. 1 is a schematic, pictorial illustration of a system for combined assessment of body fluid retention and Left-Atrial (LA) blood pressure, in accordance with an embodiment of the present invention.

Embodiments of the present invention that are described herein provide improved methods and systems for assessing body fluid retention, and/or changes in body fluid retention levels over time, using inductive coupling of an Alternating-Current (AC) magnetic field. In some embodiments, body fluid retention assessments are combined with Left-Atrial (LA) blood pressure measurements to provide reliable detection of abnormalities, e.g., Heart Failure (HF) deterioration that warrants hospitalization.

In some embodiments, a medical system comprises (i) an electronic device positioned in a patient's body, e.g., in a cardiac implant, and (ii) an external unit configured to be worn by the patient and to interact with the electronic device.

The external unit comprises a magnetic-field transducer and associated circuitry. The magnetic-field transducer, e.g., a coil, is coupled externally to the patient body, e.g., fitted in a belt that surrounds the patient thorax. The circuitry is configured to generate and apply to the magnetic-field transducer a time-varying signal, so as to generate a time-varying magnetic field. The magnetic field is used for supplying electrical energy to the electronic device in the implant, by inductive coupling. In some embodiments the magnetic field is also used for communicating with the electronic device.

In some embodiments, the circuitry in the external unit is configured to estimate the intensity of the magnetic field that reaches the electronic device, and to assess the amount of fluid retention in an organ of the patient, e.g., in the patient's lungs, based on the estimated intensity of the magnetic field. If the fluid retention is indicative of an abnormality, the circuitry may initiate an alert or other suitable responsive action.

The disclosed medical system can also be viewed as a transformer, in which the magnetic-field transducer of the external unit serves as the primary coil, and an antenna of the implant serves as the secondary coil (or vice versa). The circuitry in the external unit is configured to estimate a measure of the magnetic-field inductive-coupling between the primary coil and the secondary coil of the transformer, and to assess the fluid retention level based on the estimated measure of the magnetic-field inductive-coupling.

In some embodiments, the electronic device in the implant acquires Left-Atrial (LA) blood pressure measurements in the patient's heart. The electronic device transmits the measurement results to the external unit using load modulation, i.e., by modulating the load of its antenna. The external unit receives and decodes the LA blood pressure measurements by sensing the modulation applied to the magnetic field. The external unit may analyze the body fluid retention measurements and the LA blood pressure measurement jointly, so as to detect abnormalities with high sensitivity and low false-alarm probability.

The external unit may use various techniques for estimating the intensity of the magnetic field that reaches the electronic device in the implant. In one embodiment, the electronic device in the implant sends to the external unit explicit data indicative of the intensity of the magnetic field it senses. This data may comprise, for example, a data word specifying the intensity with some predefined precision, or a single bit that indicates whether the intensity exceeds a predefined threshold. In other embodiments, the external unit measures the intensity of the magnetic field while the implant is transmitting using load modulation. This measurement is indicative of the amount of energy that the implant is drawing from the externally-applied magnetic field. In yet other embodiments, the external unit performs an iterative process that measures the minimal magnetic-field intensity needed for invoking response from the implant. Any of these techniques, or any other suitable technique, can be used for estimating the intensity of the magnetic field that reaches the electronic device in the implant, and to use this estimation for assessing fluid retention in the patient body.

Some of the disclosed techniques use explicit cooperation of the implant for fluid retention measurements. Other disclosed techniques do not require that the implant be designed to support fluid retention assessment. The latter techniques are useful, for example, for assessing fluid retention using implants that are already implanted in patients, and/or legacy implants that were designed for other purposes, e.g., solely for intra-cardiac blood pressure sensing.

Various conditions can be specified for detecting abnormal conditions, e.g., HF deterioration. In one non-limiting example, the external unit identifies a consistent increase in LA pressure over a certain time period, which is followed by increased fluid retention. Such a sequence of events can only be identified using a combination of LA pressure measurements and fluid retention measurements, and is indicative with very high probability of HF deterioration that requires urgent attention.

The disclosed techniques exploit the same magnetic field and the same induction coupling mechanism, which are used for powering the electronic device (e.g., implant), for assessing fluid retention. As such, the disclosed solution is simple to implement and does not require any additional dedicated hardware.

System Description

FIG. 1 is a schematic, pictorial illustration of a system 20 for combined assessment of body fluid retention and Left-Atrial (LA) blood pressure, in accordance with an embodiment of the present invention. System 20 comprises an implant 24 that is implanted at a desired location in a heart 28 of a patient 30, and is used for measuring the ambient blood pressure in its vicinity. In an example embodiment, implant 24 is implanted across the interatrial septum of heart 28, and is configured to measure the blood pressure in the Left Atrium (LA).

System 20 further comprises an external unit 32, which is configured to communicate with implant 24 and to provide electrical power to the implant's circuitry. In the present example, external unit 32 is fitted on a belt that is worn by the patient. The belt also comprises an antenna coil 33 of the external unit that surrounds the patient's thorax. In the present example the belt is worn diagonally over the neck and one shoulder of the patient. Alternatively, however, any other suitable configuration can be used.

Implant 24 typically does not comprise an internal power source. The internal circuitry of the implant is powered by energy that is provided by external unit 32 using inductive coupling. Typically, the external unit generates an Alternating Current (AC) magnetic field via antenna coil 33. This magnetic field induces an AC voltage across an antenna of the implant, and this voltage is then rectified and used for powering the implant circuitry. At the same time, the implant sends data (e.g., measurement results of ambient blood pressure) by modulating the load impedance of its antenna, modulation that is sensed by the external unit.

An inset on the right-hand side of FIG. 1 shows the mechanical structure of implant 24. In this example embodiment, implant 24 comprises an elongated tube 34 that comprises the electronic circuitry of the implant. Tube 34 is inserted into the interatrial septum. A "septum gripper" 40, comprising a collapsible and extensible mesh, is used for fixating tube 34 to the septum. An antenna coil 36 and a pressure sensor 38 are fitted on opposite sides of tube 34. Implant 24 is implanted such that pressure sensor 38 is positioned in the left atrium and antenna 36 is in the right atrium.

Implants of this sort are addressed in greater detail in U.S. Patent Application Publication 2018/0110468, entitled "Heart Implant with Septum Gripper" and in U.S. Patent Application Publication 2018/0098772, entitled "Deploying and Fixating an Implant Across an Organ Wall," which are assigned to the assignee of the present patent application and whose disclosures are incorporated herein by reference.

Further aspects of blood pressure measurement using such implants, and of interaction between implants and external units using magnetic-field inductive coupling, are addressed, for example, in U.S. Patent Application Publication 2015/0282720, entitled "Drift Compensation for Implanted Capacitance-Based Pressure," in U.S. Pat. No. 10,105,103, entitled "Remotely Powered Sensory Implant," in U.S. Patent Application Publication 2019/0008401, entitled "Power-Efficient Pressure-Sensor Implant," and in U.S. Pat. No. 10,205,488, entitled "Low-Power High-Accuracy Clock Harvesting in Inductive Coupling Systems." All these patents and patent applications are assigned to the assignee of the present patent application and their disclosures are incorporated herein by reference.

Assessment of Body Fluid Retention Using Inductive Coupling

Figure 2:
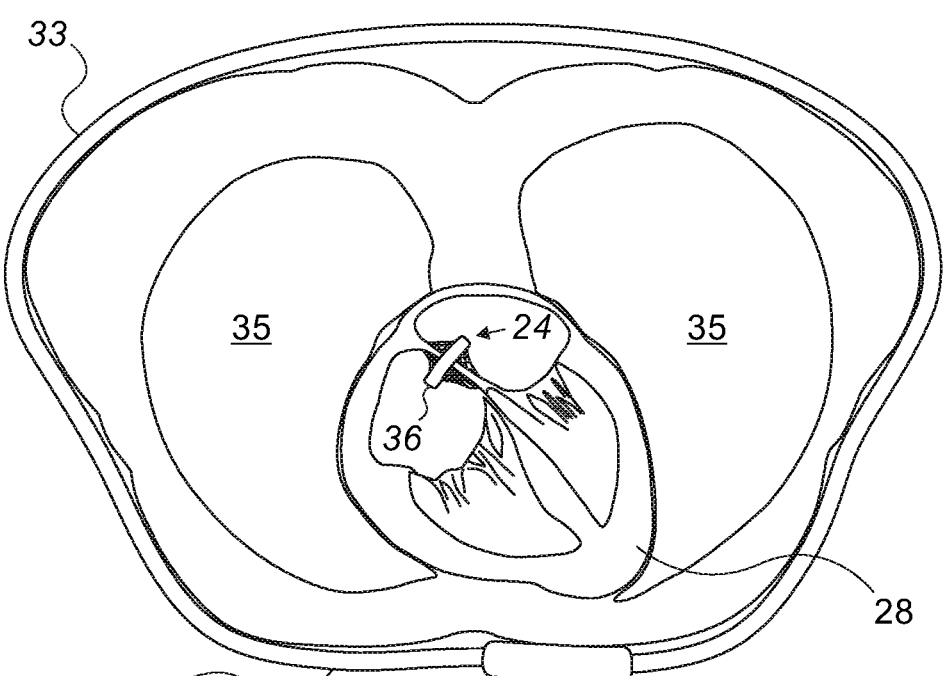
FIG. 2 is a schematic cross-section of a thorax of a patient undergoing assessment of body fluid retention and LA blood pressure, in accordance with an embodiment of the present invention.

FIG. 2 is a schematic top-view cross-section of a thorax of a patient undergoing assessment of body fluid retention and LA blood pressure using system 20, in accordance with an embodiment of the present invention. The top-view cross-section shows heart 28 of the patient, with implant 24 fitted therein. Antenna coil 36 of implant 24 is specifically marked. Also seen are lungs 35 of the patient. The patient wears external unit 32 with antenna coil 33 surrounding his/her thorax.

During a measurement session, coil 33 applies an AC magnetic field, which induces a voltage in antenna coil 36 of implant 24. As can be appreciated, the intensity of the magnetic field that reaches implant 24 depends on the properties of the tissue between coil 33 and coil 36. Specifically, high fluid content in the volume between coil 33 and coil 36 causes higher attenuation to the magnetic field, and the intensity of the magnetic field reaching the implant will be lower. By the same token, low fluid content in the volume between coil 33 and coil 36 causes the intensity of the magnetic field reaching the implant to be higher.

The fluid affecting the magnetic field may comprise, for example, fluid in lungs 35 and/or fluid retained in any other organ or tissue between coil 33 (of the external unit) and coil 36 (of the implant). A non-limiting list of example medical conditions that can be detected using the disclosed techniques includes the following:

Cardiac tamponade—accumulation of fluid in the pericardial space.

Pulmonary edema—fluid collected within the air sacs in the lungs, within the parenchyma.

Pleural effusion—fluid collected in the layers of the pleura outside the lungs—within the pleural cavity.

Aortic dissection—injury to the innermost layer of the aorta, allowing blood to build up between the layers of the aortic wall. Various other types of hemorrhage can also be detected. In the present context, blood build-up is also regarded herein as fluid retention.

Abscess—pockets of infected fluid.

By estimating the intensity of the magnetic field that reaches implant 24, external unit 32 is able to assess the level of fluid retention. Moreover, the intensity of the magnetic field that reaches implant 24 serves as a single figure-of-merit, which integrates the fluid retention level across the entire volume of interest. As such, the disclosed solution does not require complicated imaging and signal processing.

The view of FIG. 2 demonstrates that system 20 can be viewed as a transformer, in which coil 33 of external unit 32 serves as the primary coil, and antenna 36 of implant 24 serves as the secondary coil (or vice versa). The circuitry in external unit 32 is configured to estimate a measure of the magnetic-field inductive-coupling between the primary coil and the secondary coil of this transformer, and to assess the fluid retention level based on the estimated measure of the magnetic-field inductive-coupling.

The view of FIG. 2 also shows the "near-field" characteristic of the disclosed techniques. As seen in the figure, both the tissue in which fluid retention is being assessed, and the electronic device in implant 36 used in the measurement, are in the near-field region of external coil 33. One commonly-used definition of "near-field region" is that the distance between coil 33 and the tissue or implant is smaller than $2D^2/\lambda$, wherein D denotes the characteristic dimension (e.g., diameter) of coil 33, and $\lambda$ denotes the wavelength of the AC signal being used.

Implant and External Unit Circuitry

Figure 3:
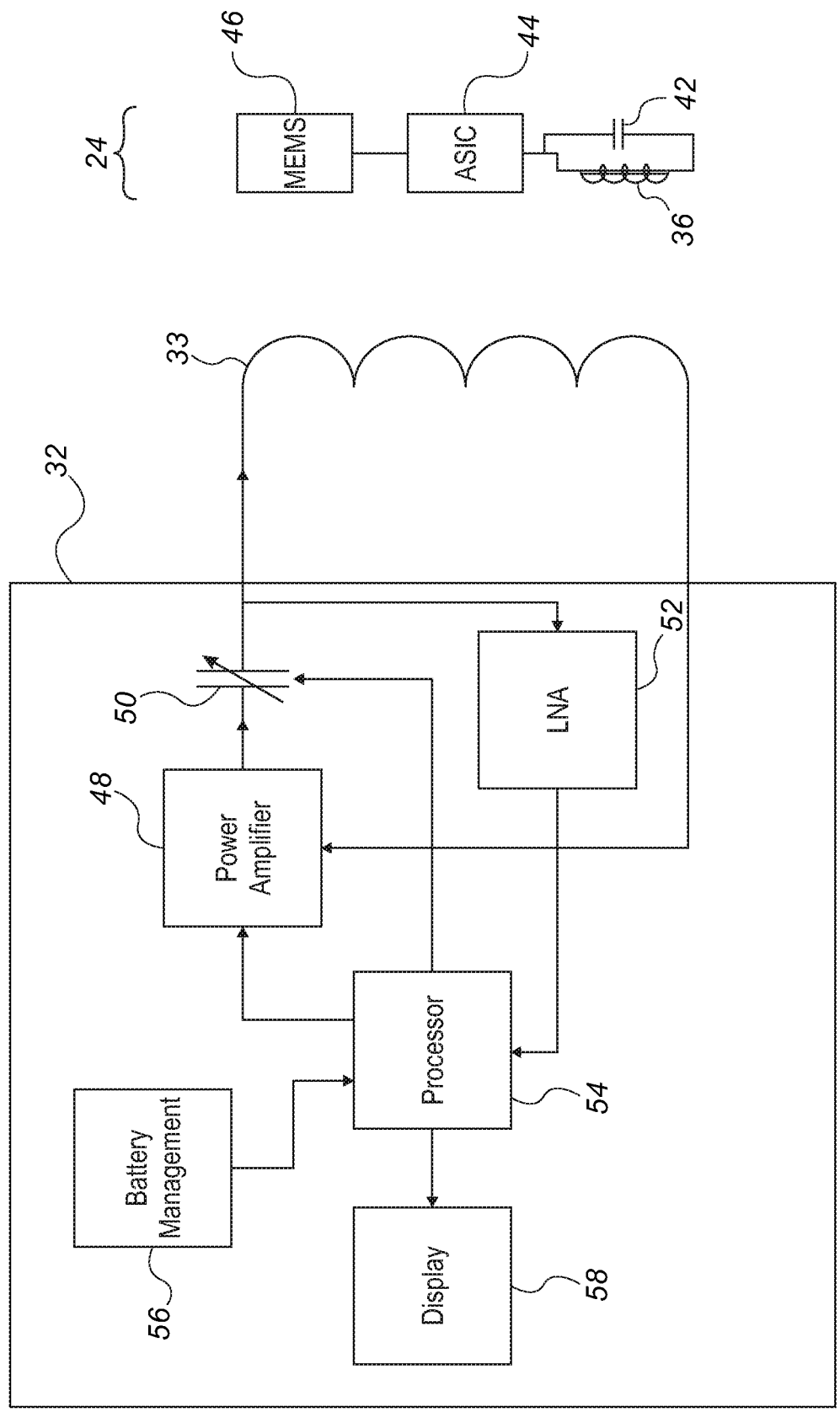
FIG. 3 is a block diagram that schematically illustrates the system of FIG. 1, in accordance with an embodiment of the present invention.

FIG. 3 is a block diagram that schematically illustrates system 20, in accordance with an embodiment of the present invention. Implant 24 is illustrated on the right-hand side of the figure, and external unit 32 is depicted on the left-hand side.

In the example of FIG. 3 implant 24 comprises antenna coil 36 and a capacitor 42. Coil 36 and capacitor 42 together form a resonant circuit, whose resonant frequency matches the frequency of the AC magnetic field applied by external unit 32. In the present example this frequency is 6.78 MHz, although any other suitable frequency can be used. Implant 24 further comprises a mixed-signal Application-Specific Integrated Circuit (ASIC) 44, and a Micro Electro Mechanical System (MEMS) pressure sensor 46. The internal structure of implant 24, and especially the structure of ASIC 44, is shown in greater detail in FIG. 4 below.

In the example of FIG. 3, external unit 32 comprises a Power Amplifier (PA) 48, a variable capacitor 50, a Low-Noise Amplifier (LNA) 52, a processor 54, a display 58 and a battery management circuit 56. All these components are referred to collectively as the circuitry of the external unit. In alternative embodiments, any other suitable circuitry can be used.

In an embodiment, processor 54 generates an AC signal (e.g., a square or sinusoidal waveform) at the desired frequency of the AC magnetic field (in the present example 6.78 MHz). PA 48 amplifies the AC signal and drives antenna coil 33 with the amplified signal.

Coil 33 and variable capacitor 50 together form a resonant circuit, whose resonant frequency matches the frequency of the AC magnetic field. The capacitance of variable capacitor is controlled by processor 54, to compensate for variations in the inductance of coil 33 that may be caused by the patient body.

LNA 52 senses the voltage on coil 33, and amplifies the sensed voltage. The output of LNA 52 is provided as a reception signal to processor 54, for receiving data from implant 24. In this embodiment, ASIC 44 in implant 24 transmits data to external unit 32 by modulating the load impedance of antenna coil 36. The load modulation in turn modulates the extent of dissipation of the magnetic field in the implant. As a result, the load modulation in implant 24 modulates the voltage on coil 33 of the external unit. LNA 52 thus senses and amplifies this modulated signal, and processor 54 decodes the signal and recovers the data sent by the implant. As will be explained below, this data may comprise, for example, LA blood pressure readings derived from measurements of MEMS sensor 46, and/or data indicative of the intensity of the magnetic field reaching the implant, for use in fluid retention assessment.

Battery management circuit 56 is responsible for the various power-supply functions of external unit 32. Display 58 is used by processor 54 for displaying information to the patient or to other users, e.g., to a physician. Displayed information may comprise, inter alia, alerts and/or other information relating to LA blood pressure and/or fluid retention assessment.

Figure 4:
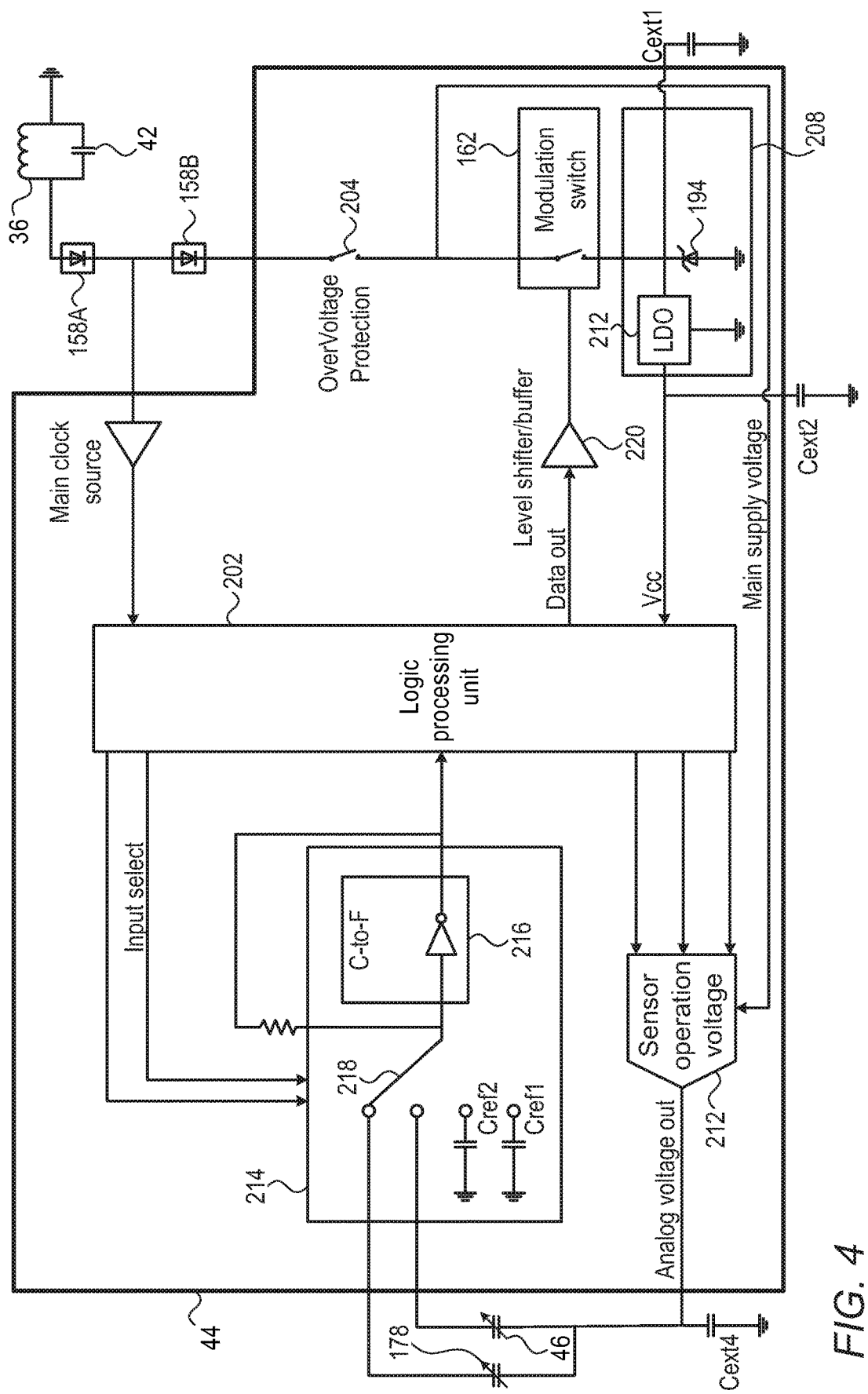
FIG. 4 is a block diagram that schematically illustrates an internal structure of an implant in the system of FIGS. 1 and 3, in accordance with an embodiment of the present invention.

FIG. 4 is a block diagram that schematically illustrates the internal structure of implant 24, in accordance with an embodiment of the present invention. In the present embodiment, most of the circuitry of implant 24 is implemented in mixed-signal ASIC 44. Some elements, e.g., pressure sensor 46, a reference sensor 178, antenna coil 36 and capacitor 42, rectifiers 158A and 158B, and several capacitors, are typically external to the ASIC.

In the present example, ASIC 44 comprises a logic processing unit 202 that controls the ASIC operation. A modulator 214 comprises a Capacitance-to-Frequency (C-to-F) converter 216, which produces a square wave whose frequency depends on the input capacitance. An input selection switch 218 selects among several capacitances that can be provided as input to the C-to-F converter.

In the present example, switch 218 selects among real MEMS pressure sensor 46 (which measures the ambient blood pressure), reference MEMS pressure sensor 178, and two fixed reference capacitors denoted Cref1 and Cref2. Switch 218 is controlled by unit 202 using "INPUT SELECT" lines.

A sensor operation voltage module 212, typically comprising a digital-to-analog converter, provides a suitable analog operation voltage for the MEMS pressure sensors. The analog voltage is adjusted by unit 202, for example using discrete control lines to module 212. One reason for adjusting this voltage is as part of a drift compensation process, as described in U.S. Patent Application Publication 2015/0282720, cited above.

For data transmission from the implant, logic processing unit 202 produces a data word denoted "data out," whose value depends the output of C-to-F converter 216. In other words, "data out" is a multi-bit word that is indicative of the capacitance of the MEMS pressure sensor (or other capacitance selected by switch 218). A level shifter/buffer 220 buffers the signal and drives modulation switch 162. The load impedance of antenna coil 36 is thus modulated in accordance with the data word, as explained above. Additionally or alternatively, processing unit 202 may use the load modulation mechanism for transmitting one or more data bits indicative of the intensity of the magnetic field reaching implant 24. This data may be used by external unit 32 for assessing fluid retention.

For providing electrical power to ASIC 44, rectifiers 158A and 158B rectify the AC voltage induced in antenna coil 36. An over-voltage protection switch 204 protects the ASIC from high-voltage surges. The rectified voltage is regulated by a regulation unit 208. In unit 208, the voltage is clamped by clamping element 194. An external capacitor denoted Cext1 serves as energy backup element (similar to element 198 of FIG. 7). A low Drop-Off (LDO) regulator 212 further regulates the supply voltage. The output of LDO regulator 212 is provided as the supply voltage (Vcc) of ASIC 44.

Voltage clamping element 194 in unit 208 plays a dual role—Maximizes the modulation depth of the load modulation scheme, and regulates the supply voltage for ASIC 44. A "main clock source" module derives a clock signal for the ASIC from the induced AC voltage. In an alternative embodiment, the main clock source may be generated by the ASIC.

The configurations of system 20 and its elements, including implant 24 and external unit 32 and their various components, as depicted in FIGS. 1, 3 and 4, are example configurations that are shown purely for the sake of conceptual clarity. In alternative embodiments, any other suitable configuration can be used. For example, some of the functions of processor 54 of external unit 32 may be carried out by a processor or system separate from the external unit. In one example implementation, processor 54 is configured to communicate with a patient-care system, e.g., a cloud-based system or an application running on a smart-phone of the patient. In this example, processor 54 is responsible for extracting raw LA pressure estimates and fluid retention estimates, and to transmit the estimates to the patient-care system. The patient-care system is responsible for performing higher-level tasks, such as interpreting the estimates, detecting abnormal conditions and triggering responsive actions. Further alternatively, any other suitable division of labor among system elements can be used.

In the context of the present patent application and in the claims, the term "circuitry" refers to any and all electronic circuitry of the external unit. The term "electronic device" refers to any and all electronic circuitry that is positioned in the patient body and is powered by the magnetic field generated by the external unit. In alternative embodiments, the circuitry of the external unit, and/or the electronic device, may be implemented in any other suitable way. Elements that are not necessary for understanding the principles of the present invention have been omitted from the figures for clarity.

The different elements of implant 24 and external unit 32 may be implemented using any suitable hardware, such as in one or more Application-Specific Integrated Circuits (ASICs), one or more Field-Programmable Gate Arrays (FPGAs), and/or one or more discrete components. In some embodiments, some elements of implant 24 and/or external unit 32 can be implemented using software, or using a combination of hardware and software elements.

In some embodiments, some or all of the functions of processor 54 are implemented by one or more programmable processors, which are programmed in software to carry out the functions described herein. The software may be downloaded to the processor or processors in electronic form, over a network, for example, or it may, alternatively or additionally, be provided and/or stored on non-transitory tangible media, such as magnetic, optical, or electronic memory.

Combined Assessment of Body Fluid Retention and La Blood Pressure

As noted above, in some embodiments processor 54 in external unit 32 is configured to estimate the intensity of the magnetic field that reaches implant 24, and to assess the amount of fluid retention, e.g., in lungs 35, based on the estimated intensity of the magnetic field. In various embodiments, processor 54 may use various techniques for estimating the intensity of the magnetic field that reaches implant 24.

In some embodiments, ASIC 44 in implant 24 measures the intensity of the magnetic field sensed by antenna 36. ASIC 44 then sends to external unit 32 data that is indicative of the magnetic field intensity. In one embodiment, ASIC 44 measures the voltage that is induced in antenna 36 by the magnetic field, and sends to external unit 32 data that is indicative of the sensed voltage. ASIC 44 may measure, for example, the peak-to-peak voltage of the signal at the input of the "main clock source" module (FIG. 4), i.e., the signal from which the ASIC reconstructs a clock signal. Alternatively, ASIC 44 may assess the amount of energy being received. Any other suitable measurement technique can also be used.

In an example embodiment, ASIC 44 compares the sensed voltage to a predefined threshold, and sends to external unit 32 a single bit that indicates whether the sensed voltage exceeds the threshold or not. In another example embodiment, ASIC 44 may generate and transmit a multi-bit value indicative of the voltage induced in antenna 36, e.g., by comparing the sensed voltage to two or more predefined threshold. ASIC 44 may transmit the data indicative of the magnetic-field intensity in various ways. In one example, the ASIC transmits this data using load modulation, as part of the data word that indicates the sensed LA blood pressure.

In other embodiments, processor 54 in external unit 32 may estimate the intensity of the magnetic field that reaches implant 24, without receiving any explicit indication or measurement result from the implant. In an example embodiment, processor 54 measures the voltage on coil 33 (of the external unit) while ASIC 44 (of the implant) is transmitting a pressure measurement using load modulation. Processor 54 may perform this measurement, for example, by measuring the signal provided by LNA 52. Processor 54 may measure the load-modulated signal in coil 33 during the ON times of the implant's modulation switch, during the OFF times of the modulation switch, or both (e.g., without any synchronization to the modulation). The level of the load-modulated signal in coil 33 is indicative of the intensity of the magnetic field that reaches implant 24.

In another embodiment, the implant is entirely passive and comprises a resonant circuit whose resonant frequency is indicative of the ambient blood pressure. In this embodiment, external unit 32 may apply a broadband magnetic-field, e.g., by applying to coil 33 a voltage pulse that approximates an impulse response. In response to such a magnetic field, the resonant circuit resonates, causing a spectral peak in the voltage on coil 33. In an embodiment, processor 54 estimates the level of the spectral peak on coil 33 (via LNA 52) and uses this level as an estimate for the intensity of the magnetic field that reaches the implant.

In yet another example embodiment, processor 54 estimates the intensity of the magnetic field that reaches implant 24 by performing an iterative process that gradually increases the power of the applied AC magnetic field, until the implant begins to respond. The power level of the magnetic field that invokes initial reaction from the implant is indicative of the magnetic-field absorption in the intermediate tissue, and thus indicative of fluid retention level.

Further alternatively, processor 54 may use any other suitable technique for estimating the intensity of the magnetic field that reaches implant 24, and for using this estimation for assessing fluid retention in the body of patient 30.

Figure 5:
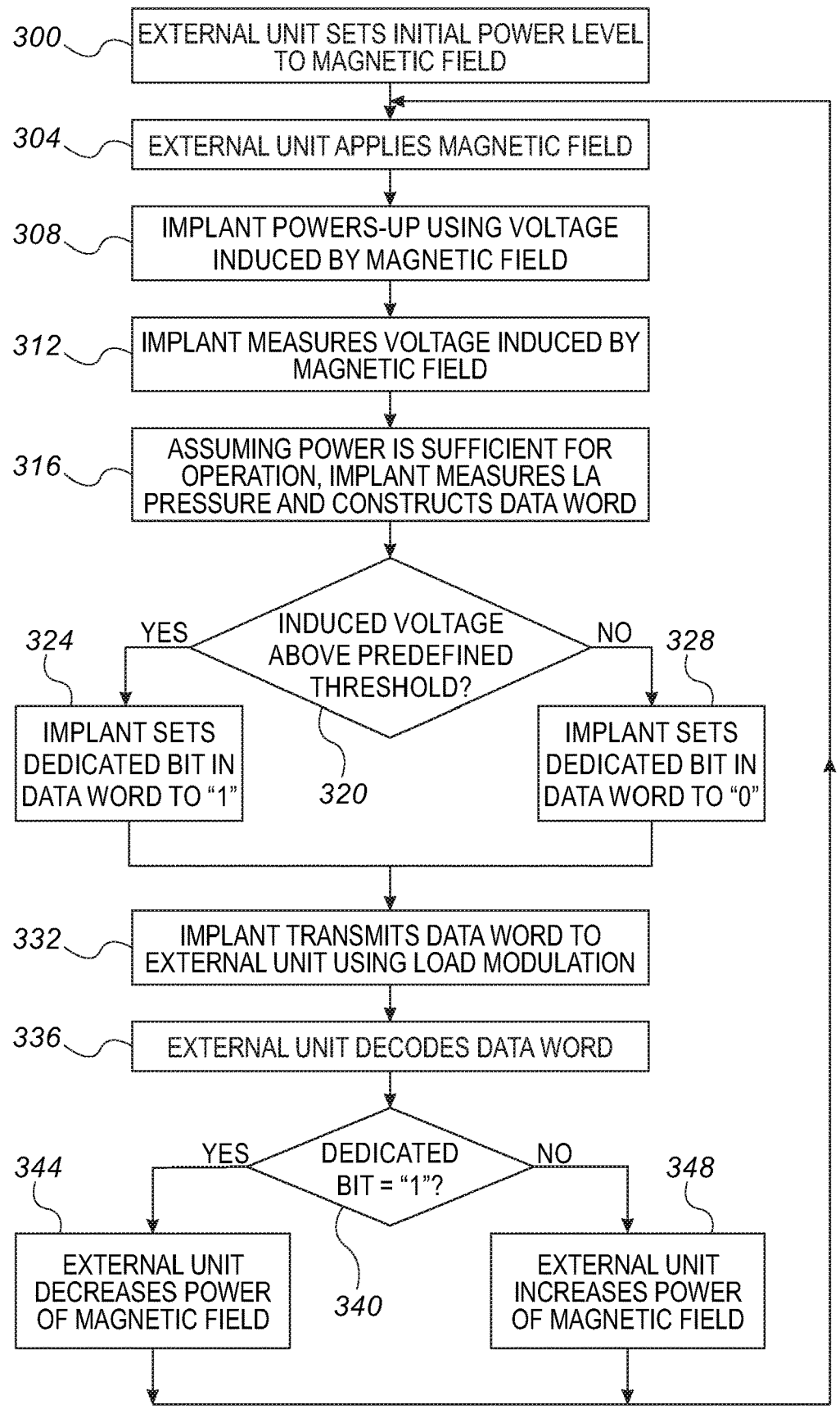
FIGS. 5 and 6 are flow charts that schematically illustrate methods for combined assessment of body fluid retention and LA blood pressure, in accordance with embodiments of the present invention.

FIG. 5 is a flow chart that schematically illustrates a method for combined assessment of body fluid retention and LA blood pressure, in accordance with an embodiment of the present invention. The method begins with processor 54 of external unit 32 setting an initial power level for the AC magnetic field to be applied to implant 24, at an initialization step 300.

At a magnetic-field application step 304, processor 54 and PA 48 apply the magnetic field. At a power-up step 308, the circuitry of implant 24, e.g., ASIC 44, powers-up using the voltage that is induced in antenna 36 by the magnetic field.

At a voltage measurement step 312, the circuitry in implant 24 senses the level of the induced voltage in antenna 36. Assuming the power level of the magnetic field is sufficient for proper operation of implant 24, the circuitry in the implant senses the ambient LA pressure, and constructs a data word indicative of the sensed pressure, at a pressure measurement step 316.

At a comparison step 320, the circuitry in implant 24 compares the induced voltage to a predefined threshold. If the induced voltage is above the predefined threshold, the circuitry in implant 24 sets a dedicated bit in the data word to "1", at a bit assertion step 324. Alternatively, if the induced voltage is not above the predefined threshold, the circuitry in implant 24 sets the dedicated bit in the data word to "0", at a bit de-assertion step 328.

At a transmission step 332, the circuitry in implant 24 transmits the data word to external unit 32 using load modulation, by modulating the load impedance of antenna 36. At a decoding step 336, processor 54 in external unit 32 receives the load-modulated signal via LNA 52, and decodes the data word.

At a bit checking step 340, processor 54 checks the value of the dedicated bit. If the dedicated bit value is "1" (meaning that the magnetic-field reaching implant 24 was above the predefined threshold), processor 54 decreases the power of the magnetic field, at a power decreasing step 344. If the dedicated bit value is "0" (meaning that the magnetic-field reaching implant 24 was not above the predefined threshold), processor 54 increases the power of the magnetic field, at a power increasing step 348. The method then loops back to step 304 above.

Typically, system 20 continues the process of FIG. 5 until converging to a stable power level of the applied magnetic field. This stable power level is indicative of the extent of absorption of the tissue between coil 33 (in the external unit) and antenna 36 (in the implant), and therefore indicative of the fluid retention level in the body of patient 30 (e.g., in lungs 35).

In some embodiments, processor 54 specifies a condition that depends on (i) one or more pressure measurements, and (ii) one or more fluid retention level measurements, and that is indicative of an abnormal condition that requires attention. Upon detecting such a condition, processor 54 initiates a responsive action, e.g., triggers an alert. Additionally or alternatively, any other suitable condition can be specified and checked for.

Figure 6:
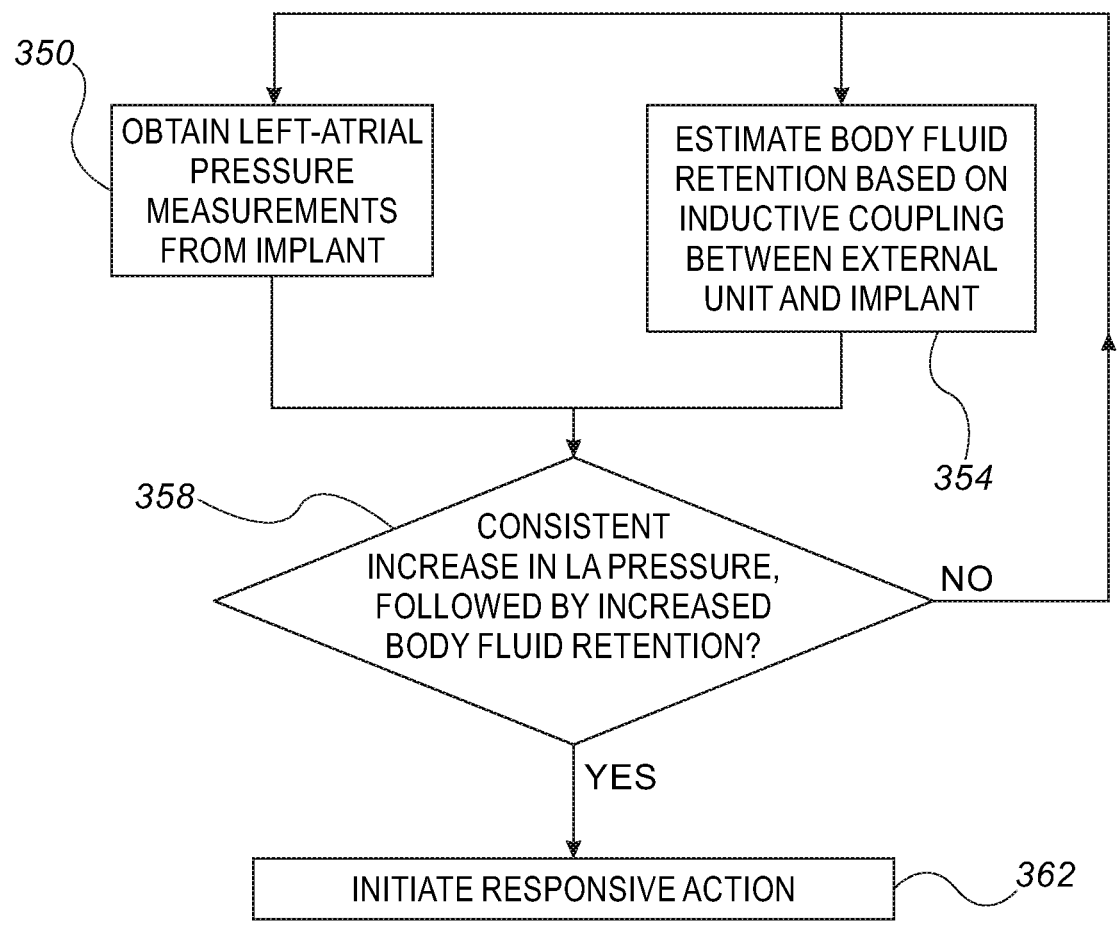

FIG. 6 is a flow chart that schematically illustrates a method for combined assessment of body fluid retention and LA blood pressure, in accordance with an embodiment of the present invention. The method begins with processor 54 obtaining a sequence of LA pressure measurements from implant 24, at a pressure obtaining step 350. At a fluid retention estimation step 354, processor 54 produces one or more estimates of fluid retention level, using any of the techniques described herein.

At a condition evaluation step 358, processor 54 checks for a consistent trend of increasing LA pressure over a certain time period (e.g., two weeks), which is followed by an increase in fluid retention. If the condition is met, processor 54 initiates a responsive action, at a response initiation step 362. Otherwise, the method loops back to repeat steps 350 and 354 above.

The method flows shown in FIGS. 5 and 6 are example flows that are chosen purely for the sake of conceptual clarity. In alternative embodiments, any other suitable flows can be used for implementing the disclosed techniques.

Although the embodiments described herein mainly address implants that are located in the heart and measure LA pressure, the methods and systems described herein are in no way limited to such implants. In alternative embodiments, the disclosed techniques can be implemented by interacting with various intra-body electronic devices in various other medical devices positioned at various other positions in a patient body. Such electronic devices may or may not measure ambient pressure, in addition to serving for fluid retention estimation. Alternatively to implants, such intra-body electronic devices may be fitted, for example, in catheters or other probes. Alternatively to the left atrium, such intra-body electronic devices may be positioned, for example, elsewhere in the patient's cardiovascular system, e.g., in a pulmonary artery, or even in the esophagus.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   a magnetic-field transducer, which is configured to be coupled externally to a body of a patient; and
   circuitry, configured to:
     generate and apply to the magnetic-field transducer a time-varying signal, thereby generating a time-varying magnetic field that supplies electrical energy by inductive coupling to an electronic device that is positioned inside the body;
     identify a response of the electronic device to the magnetic field, the response being a function of an intensity of the magnetic field that reaches the electronic device; and
     assess fluid retention in an organ of the patient based on the response.

2. The apparatus according to claim 1, wherein the circuitry is configured to initiate a responsive action upon detecting that the fluid retention is indicative of an abnormality.

3. The apparatus according to claim 1, wherein the organ comprises a lung of the patient.

4. The apparatus according to claim 1, wherein the response includes data indicative of the intensity of the magnetic field that reaches the electronic device, and wherein the circuitry is configured to assess the fluid retention based on the data.

5. The apparatus according to claim 4, wherein the data comprises an indication of whether the intensity of the magnetic field exceeds a predefined threshold.

6. The apparatus according to claim 4, wherein the circuitry is configured to assess the fluid retention by adaptively adjusting a power level of the signal applied to the magnetic-field transducer depending on the data.

7. The apparatus according to claim 1,
   wherein the circuitry is configured to adaptively adjust a power level of the signal applied to the magnetic-field transducer so as to identify a minimal power level that invokes the response from the electronic device, and wherein the circuitry is configured to assess the fluid retention based on the minimal power level.

8. The apparatus according to claim 1,
wherein the response includes a modulation of the induction-coupled magnetic field, and
wherein the circuitry is configured to assess the fluid retention by measuring the modulated magnetic field outside the body.

9. The apparatus according to claim 1,
wherein the response includes a resonation at a frequency that is indicative of the intensity, and
wherein the circuitry is configured to assess the fluid retention by measuring the magnetic field outside the body while the electronic device is resonating.

10. The apparatus according to claim 1, wherein the circuitry is configured to receive from the electronic device one or more blood pressure measurements in a heart of the patient, and to initiate a responsive action upon detecting that a combination of the fluid retention and the blood pressure measurements is indicative of an abnormality.

11. A method, comprising:
generating a time-varying signal and applying the time-varying signal to a magnetic-field transducer coupled externally to a body of a patient, thereby generating a time-varying magnetic field that supplies electrical energy by inductive coupling to an electronic device that is positioned inside the body;
identifying a response of the electronic device to the magnetic field, the response being a function of an intensity of the magnetic field that reaches the electronic device; and
assessing fluid retention in an organ of the patient based on the response.

12. The method according to claim 11, further comprising initiating a responsive action upon detecting that the fluid retention is indicative of an abnormality.

13. The method according to claim 11, wherein the organ comprises a lung of the patient.

14. The method according to claim 11, wherein the response includes data indicative of the intensity of the magnetic field that reaches the electronic device, and wherein assessing the fluid retention comprises assessing the fluid retention based on the data.

15. The method according to claim 14, wherein the data includes an indication of whether the intensity of the magnetic field exceeds a predefined threshold.

16. The method according to claim 14, wherein assessing the fluid retention comprises adaptively adjusting a power level of the signal applied to the magnetic-field transducer depending on the data.

17. The method according to claim 11, wherein applying the time-varying signal to the magnetic-field transducer comprises adaptively adjusting a power level of the signal so as to identify a minimal power level that invokes the response from the electronic device, and wherein assessing the fluid retention comprises assessing the fluid retention based on the minimal power level.

18. The method according to claim 11,
wherein the response includes a modulation of the induction-coupled magnetic field, and
wherein assessing the fluid retention comprises assessing the fluid retention by measuring the modulated magnetic field outside the body.

19. The method according to claim 11,
wherein the response includes a resonation at a frequency that is indicative of the intensity, and
wherein assessing the fluid retention comprises assessing the fluid retention by measuring the magnetic field outside the body while the electronic device is resonating.

20. The method according to claim 11, further comprising receiving from the electronic device one or more blood pressure measurements in a heart of the patient, and initiating a responsive action upon detecting that a combination of the fluid retention and the blood pressure measurements is indicative of an abnormality.

* * * * *